United States Patent [19]
Zsolnai et al.

[11] 4,058,608
[45] Nov. 15, 1977

[54] METHOD OF TREATING FUNGUS-INFECTED PLANTS WITH PHENYLAZOCYANOACETIC ESTER DERIVATIVES

[75] Inventors: Tibor Zsolnai, Debrecen; György Lugosi, Felsogod; István Szepesi, Debrecen; Maria Bakonyi, Budapest; István Rácz, Budapest; Erzsébet Radvány nee Hegedüs, Budapest, all of Hungary

[73] Assignee: Chinoin Gyogyszer es Vegyeszeti Termekek Gyara RT, Budapest, Hungary

[21] Appl. No.: 624,774

[22] Filed: Oct. 20, 1975

[30] Foreign Application Priority Data

Oct. 24, 1974 Hungary .............................. CI 1515

[51] Int. Cl.² .............................................. A01N 9/20
[52] U.S. Cl. .................................... 424/226; 424/304
[58] Field of Search ................................ 424/226, 304

[56] References Cited

U.S. PATENT DOCUMENTS 2,489,927  11/1949  Pfister et al. .......................... 260/482
3,839,564  10/1974  Wright et al. .......................... 424/226

OTHER PUBLICATIONS

Schrotter et al., "Pharmazie" 27/2 (1972), pp. 93-94.
Biochem. Pharm., 13 (1964), pp. 285-318.

Primary Examiner—V. D. Turner
Attorney, Agent, or Firm—Karl F. Ross

[57] ABSTRACT

The invention relates to a method of combatting phytopathogenic fungi, primarily powdery mildew. The method involves administering compositions according to the invention which contain as active principle at least one compound of the formula (I),

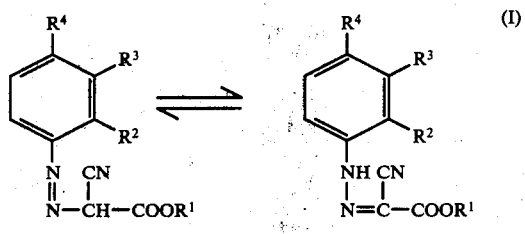

wherein
$R^1$ is a $C_{1-12}$ alkyl or a chloroethyl group,
$R^2$ is hydrogen, halogen, a $C_{1-4}$ alkyl, a $C_{1-4}$ alkoxy or nitro group,
$R^3$ is hydrogen, halogen, a $C_{1-4}$ alkyl or nitro group, and
$R^4$ is hydrogen, halogen, a $C_{1-4}$ alkyl or nitro group, or an acid addition salt thereof.

2 Claims, No Drawings

METHOD OF TREATING FUNGUS-INFECTED PLANTS WITH PHENYLAZOCYANOACETIC ESTER DERIVATIVES

This invention relates to new plant-biological compositions having fungicidal effects. The new compositions according to the invention can be used primarily for combatting phytopathogeneous fungal diseases of plants, and exert both prophylactic and healing effects.

The new plant-biological compositions according to the invention contain as active principle at least one compound of the formula (I),

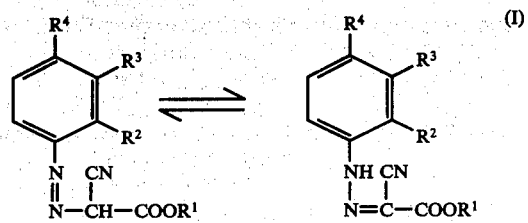

wherein
- $R^1$ is a $C_{1-12}$ alkyl or chloroethyl group,
- $R^2$ is hydrogen, halogen, $C_{1-4}$ alkoxy or nitro group,
- $R^3$ is hydrogen, halogen, $C_{1-4}$ alkyl or nitro group, and
- $R^4$ is hydrogen, halogen, $C_{1-4}$ alkyl or nitro group, or an acid addition salt thereof in an amount of 1 to 99 % by weight, along with 99 to 1 % by weight of an additive.

As it appears from the above formulae, the compounds of the formula (I) may exist in two tautomeric forms. The ratio of these tautomers is determined primarily by the pH value of the solvent medium, it depends, however, to a certain extent also on the redox potential of the medium, on the physico-chemical properties of the solvent additives and on the polar or apolar nature of the solvent medium.

The compounds of the formula (I) are known substances (U.S. Pat. Nos. 2,489,927 and 2,515,691; British patent specification No. 636,603). Those compounds of the formula (I), wherein $R^1$ stands for a $C_{1-4}$ alkyl group, are used primarily as intermediates in the synthesis of other derivatives.

The preparation of the compounds having the formula (I) in two forms, one with a higher and another with a lower melting point, is discussed in detail in Beilsteins Handbuch der Organischen Chemie (Vol. 15, pages 370 to 371). In the syntheses discussed in the cited reference generally a mixture of the two isomers is obtained.

The biological effects of some compounds falling within the scope of the formula (I) have already been examined from human pathological points of view (Biochem. Pharm. 13, 285-318 (1964). In these experiments the bacteriostatic, fungistatic, tuberculostatic, trichomonastatic and ascaricidal effects were tested under in vitro conditions, but no appreciable activities could be detected. Furthermore, these compounds have no effect on ascaris suum (Pharmazie 27/2, 93-94 (1972).

Now it has been found, unexpectedly, that although the compounds of the formula (I) are inactive against numerous fungus strains under in vitro conditions, they exert significant fungicidal effects primarily against powdery mildew when examined under in vivo conditions. As known, mildew-type fungi cannot be cultivated on artificial media, thus the antifungal effects exerted against mildew-type fungi can be examined only on the host plants under in vivo conditions.

The compounds of the formula (I) can be prepared by subjecting an amine of the formula (II),

wherein $R^2$, $R^3$ and $R^4$ each have the same meanings as defined above, to diazotization, and reacting the obtained product with a cyanoacetic ester of the formula (III),

$$CN-CH_2-COOR^1 \qquad (III)$$

wherein $R^1$ has the same meanings as defined above. If desired, the obtained product is converted into its salts.

The first step of the above-discussed synthesis is performed preferably in an aqueous medium, by contacting a phenylamine of the formula (II) with an aqueous solution of sodium nitrite in the presence of a mineral acid. Subsequently, the obtained product is treated with an alcoholic solution of a cyanoacetic ester having the formula (III). Prior to performing this latter step, the strongly acidic nature of the medium is suppressed by adding e.g. an alkali hydroxide or sodium acetate to the mixture. Alternately, an alkali metal salt of the appropriate cyanoacetic ester can be used as well. The obtained compounds separate generally in crystalline state. Some of the products, primarily those containing higher alkyl radicals, separate in oily state, these oily substances, however, also crystallize after some hours of standing. The crude products can be purified by recrystallization e.g. from methanol, ethanol, isopropanol, butanol or nitropropane. The obtained substances are yellow solids, insoluble in water but generally well soluble in organic solvents (e.g. in alcohols, dioxane, dimethyl formamide, chloroform, benzene, acetone, etc.). The melting points of the obtained substances vary to some extent depending on the preparation conditions.

The compounds of the formula (I) can be converted into plant-biological compositions with fungicidal effects. These compositions may be liquids or solids.

Liquid compositions are prepared by admixing at least one compound having the formula (I), as active agent, with at least one liquid diluent. Certain liquid diluents, such as alcohols, ketones, dioxane, dimethyl formamide, etc., dissolve the active agent, whereas when using other liquid diluents, e.g. water, sprayable paraffine oils, chlorinated hydrocarbons, etc., a suspension of the active agent is obtained. The liquid compositions contain generally 1 to 50 % of active agent. Besides the active agent, the liquid compositions may also contain surface-active agents, primarily emulsifying agents, in order to facilitate the formation of aqueous emulsions or suspensions, respectively. The compositions contain these surfactants generally in an amount less than 10%. These surface-active agents may be cationic, anionic or non-ionic compounds. Wetting agents, such as alkylated benzene- and naphthalenesulfonates, sulfonated fatty alcohols, sulfonated fatty acid esters, polyoxyethylene-fatty alcohol ethers, polyoxyethylene-fatty acid esters, sodium sulfusuccinate esters, sulfonated mineral oils, sulfonated vegetable oils, etc. can be used to great advantage.

Of the dispersing agents usable in accordance with the invention the following are to be mentioned: methyl cellulose, polyvinyl alcohol, sodium, calcium and magnesium ligninsulfonates, sodium naphthalenesulfonate, polyvinylpyrrolidone derivatives, lignin, sulfite waste liquors, etc.

The solid compositions (primarily powders) contain, besides the active ingredient, one or more solid fillers, such as natural rock flours, e.g. kaoline, clay, talc and chalk, and synthetic rock flours, such as highly disperse silicic acid and silicates as well. The finely ground powder mixtures can be used to a great advantage as powder dusts.

The solid compositions may also contain a wetting or dispersing agent. These solid compositions, i.e. the wettable powders, contain as wetting agent preferably an alkylated benzene- or naphthalenesulfonate, a sulfonated fatty alcohol, a sulfonated fatty acid ester, a polyoxyethylene-fatty alcohol ester, a polyoxyethylene-fatty acid ester, a sodium sulfosuccinate ester, a sulfonated mineral oil, a sulfonated vegetable oil, or a mixture thereof. Of the most preferred dispersing agents e.g. the following are to be mentioned: methyl cellulose, polyvinyl alcohol, sodium, calcium and magnesium ligninsulfonates, sodium naphthalenesulfonate, polyvinylpyrrolidone derivatives, lignin, sulfite waste liquor, etc.

The compositions according to the invention can be applied onto the area to be treated by conventional methods, e.g. by spraying, powdering, watering or atomizing. The compositions can also be used to a great advantage as dressing agents for the treatment of cereal grains.

The antifungal effects of the compositions according to the invention have been examined as follows:

A wheat variety sensitive towards powdery mildew was germinated in pots, and when the plants were 7 to 8 cm. high, they were contaminated with powdery mildew. The control plants were sprayed with spring water, whereas the test plants were sprayed with an aqueous suspension containing 0.1 % of active agent immediately after infection. Only one treatment was carried out. The results were evaluated one week after the treatment. The infection grade of the controls was 20 to 25%. On the basis of the results observed on the test plants it can be stated that all of the phenylazocyanoacetic esters involved ensure a certain degree of protection on wheat against powdery mildew, that is, all of them are active.

The extent of activity depends, however, also on the nature of the particular substituents. The most active members of the compounds having the formula (I) are those wherein $R^1$ is $C_{1-4}$ alkyl, $R^2$ is hydrogen, and $R^3$ and $R^4$ each represent hydrogen, chlorine or nitro. These compounds suppressed the infection grade to 2 to 5 %, whereas in the treatments performed with other compounds falling within the definition of the formula (I), infection grades of 6 to 12 % could be observed.

The compositions according to the invention proved to exert excellent effects also in field tests. In a field test performed on wheat the plants were sprayed with solutions containing 0.1 to 0.4 % of a wettable powder according to the invention (active agent content: 50%) prior to heading up, and the results were evaluated when the crops were ripe. The two upper leaves of the plants were collected and examined for Erysiphe graminis infection. These compounds having the formula (I), wherein $R^1$ is $C_{1-4}$ alkyl, $R^2$ is hydrogen, and $R^3$ and $R^4$ each represent hydrogen, chlorine or nitro, provided outstandingly good results in these tests.

Similarly excellent results were obtained in tests performed on tomato. In the test period the leaves of the controls were heavily infected with *Septoria lycopersici*. When spraying the plants three times with a spray solution containing 0.1 to 0.4 % of a wettable powder according to the invention (active agent content: 50%) the infection could be suppressed completely.

The phytotoxic effects of the compositions according to the invention were examined on wheat and on white mustard. The active agents were applied onto the plants according to spraying and sprinkling techniques. The treatments were performed with suspensions containing 0.2 % of active agent. According to our experiences none of the compounds tested exerted any phytotoxic side-effect on wheat (a characteristic representative of monocotyledons) or on white mustard (a characteristic representative of dicotyledons), either.

When dressing cereal grains with 0.1 to 0.4 % of a wettable powder according to the invention containing 50 % of active ingredient, complete protection can be achieved against wheat powdery mildew.

Besides the plant varieties listed above, the compositions according to the invention can also be used to a great advantage for the protection or treatment, respectively, of other plants, such as e.g. fruits, cucumber and ornamental plants, particularly rose.

The most active of the compounds having the formula (I) were also subjected to toxicity tests on mice. The $LD_0$ and $LD_{100}$ values were determined experimentally after intraperitoneal and oral administration, respectively, and the $LD_{50}$ values were calculated from these data according to the usual, internationally accepted calculation method. 5, 10 or 20% of active agent were suspended in 0.1% agar gel, and the obtained homogeneous suspensions were injected intraperitoneally into mice, or were administered into the stomach of the animals via a stomach tube. The animals were kept under observation for one week after a single treatment, and the toxicity data were evaluated on the basis of the percentage deaths observed in this period. The results are summarized in Table 1.

Table 1

| Substituents | | | | Toxicity values, mg./kg. after | | | | | |
|---|---|---|---|---|---|---|---|---|---|
| | | | | intraperitoneal administration | | | oral administration | | |
| $R^1$ | $R^2$ | $R^3$ | $R^4$ | $LD_0$ | $LD_{100}$ | $LD_{50}$ | $LD_0$ | $LD_{100}$ | $LD_{50}$ |
| $C_2H_5$— | H | Cl | H | 200 | 600 | 400 | 6000 | 6000 | 6000 |
| $C_2H_5$— | H | H | Cl | 200 | 600 | 400 | 6000 | 6000 | 6000 |
| n-$C_3H_7$— | H | Cl | H | 300 | 800 | 500 | 6000 | 6000 | 6000 |
| n-$C_3H_7$— | H | H | Cl | 400 | 1000 | 600 | 6000 | 6000 | 6000 |
| i-$C_3H_7$— | H | Cl | H | 300 | 800 | 500 | 6000 | 6000 | 6000 |
| i-$C_3H_7$— | H | H | Cl | 400 | 1000 | 600 | 6000 | 6000 | 6000 |
| n-$C_4H_9$— | H | Cl | H | 500 | 1000 | 800 | 6000 | 6000 | 6000 |
| n-$C_4H_9$— | H | H | Cl | 500 | 1000 | 800 | 6000 | 6000 | 6000 |

Table 1-continued

| Substituents | | | | Toxicity values, mg./kg. after | | | | | |
| --- | --- | --- | --- | --- | --- | --- | --- | --- | --- |
| | | | | intraperitoneal administration | | | oral administration | | |
| $R^1$ | $R^2$ | $R^3$ | $R^4$ | $LD_0$ | $LD_{100}$ | $LD_{50}$ | $LD_0$ | $LD_{100}$ | $LD_{50}$ |
| n-$C_4H_9$— | H | $NO_2$— | H | 400 | 800 | 600 | 6000 | 6000 | 6000 |
| n-$C_4H_9$— | H | H | $NO_2$— | 400 | 800 | 600 | 6000 | 6000 | 6000 |

The invention is elucidated in detail by the aid of the following non-limiting Examples.

EXAMPLE 1

Method (A)

0.1 moles of aniline (or 2-toluidine, 3-toluidine, 4-toluidine, 2-anisidine, 2-chloroaniline, 3-chloroaniline, 4-chloroaniline or 4-bromoaniline, respectively) are dissolved in a mixture of 80 ml. of water and 23 ml. of concentrated hydrochloric acid. If necessary, the solution is decolorized with activated carbon under heating, filtered when hot, and the filtrate is allowed to cool. Thereafter ice is added to the cold solution, and a solution of 0.1 moles of sodium nitrite in 30 ml. of water is added in small portions, within 10 to 15 minutes, to the vigorously stirred mixture. The excess of nitrous acid is decomposed with 0.1 to 0.2 g. of urea.

· 0.1 moles of a cyanoacetic ester having the formula (III) are dissolved in 200 ml. of methanol, and the solution is cooled to 2 to 3° C. This cold solution is poured into the above mixture, which still contains ice particles. Thereafter a solution of 34 g. of sodium acetate trihydrate in 60 ml. of water is poured into the vigorously stirred mixture, and stirring is continued. Most of the phenylazocyanoacetic esters prepared by this method separate as crystalline solids, some compounds, particularly those containing higher alkyl groups, may separate, however, in an oily state. These oily substances crystallize upon several hours of standing. The obtained crystalline solids are filtered off, washed thoroughly with water, dried, and recrystallized from methanol.

In the above procedure sodium acetate may be replaced by a 10 to 30% aqueous sodium hydroxide solution to adjust the pH of the mixture to a value between 3 and 4. Alternately, an alkali salt of a cyanoacetic ester having the formula (III) can be applied as well.

Method (B)

A mixture of 0.1 moles of 3,4-dichloroaniline (or 2-chloro-4-bromo-aniline, 3-chloro-4-bromo-aniline, 4-chloro-2-toluidine, 4-bromo-2-toluidine, 4-bromo-3-toluidine, 2-nitro-aniline, 3-nitro-anoline or 4-nitro-aniline, respectively), 100ml. of water and 35 ml. of 63% nitric acid is heated until a homogeneous solution is obtained. The solution is cooled to room temperature, whereupon the respective phenylamine nitrate separates as a crystalline substance. The mixture is cooled on an ice bath, and a solution of 0.1 moles of sodium nitrite in 30 ml. of water is added in small portions, within 10 to 15 minutes, to the vigorously stirred mixture. The excess of nitrous acid is decomposed with 0.1 to 0.2 g. of urea.

0.1 moles of a cyanoacetic ester having the formula (III) are dissolved in 200 ml. of methanol, and the solution is cooled to 2 to 3° C. This cold solution is poured into the above mixture, which still contains ice particles. Thereafter a solution of 68 g. of sodium acetate trihydrate in 100 ml. of water is poured into the vigorously stirred mixture, and the reaction mixture is processed as described in Method (A).

The compounds prepared according to the above methods are listed in Table 2 below.

Table 2

| $R^1$ | $R^2$ | $R^3$ | $R^4$ | Method | Yield, g. crude product | Yield, g. purified product | M.p. ° C (after recrystall.) |
| --- | --- | --- | --- | --- | --- | --- | --- |
| $CH_3$ | H | H | H | (A) | 17.5 | 15.2 | 173 |
| $CH_3$ | $CH_3$ | H | H | (A) | 15.6 | 14.4 | 174 |
| $CH_3$ | H | $CH_3$ | H | (A) | 16.6 | 15.4 | 122 |
| $CH_3$ | H | H | $CH_3$ | (A) | 19.0 | 17.1 | 137 |
| $CH_3$ | $CH_3O$ | H | H | (A) | 13.6 | 12.0 | 187 |
| $CH_3$ | Cl | H | H | (A) | 18.3 | 16.5 | 152 |
| $CH_3$ | H | Cl | H | (A) | 19.5 | 17.3 | 148 |
| $CH_3$ | H | H | Cl | (A) | 20.0 | 18.5 | 169 |
| $CH_3$ | H | H | Br | (A) | 22.5 | 20.2 | 176 |
| $CH_3$ | H | Cl | Cl | (B) | 21.1 | 19.5 | 167 |
| $CH_3$ | Cl | H | Br | (A) | 21.2 | 18.6 | 203 |
| $CH_3$ | H | Cl | Br | (B) | 20.5 | 14.7 | 192 |
| $CH_3$ | $CH_3$ | H | Cl | (B) | 19.4 | 18.0 | 215 |
| $CH_3$ | $CH_3$ | H | Br | (B) | 23.4 | 22.0 | 205 |
| $CH_3$ | H | $CH_3$ | Br | (B) | 22.4 | 19.4 | 171 |
| $CH_3$ | $NO_2$ | H | H | (B) | 22.8 | 20.7 | 142 |
| $CH_3$ | H | $NO_2$ | H | (B) | 20.5 | 17.5 | 186 |
| $CH_3$ | H | H | $NO_2$ | (B) | 21.3 | 20.0 | 227 |
| $C_2H_5$ | H | H | H | (A) | 18.2 | 16.1 | 126 |
| $C_2H_5$ | $CH_3$ | H | H | (A) | 16.6 | 14.0 | 141 |
| $C_2H_5$ | H | $CH_3$ | H | (A) | 17.2 | 15.1 | 131 |
| $C_2H_5$ | H | H | $CH_3$ | (A) | 18.3 | 16.0 | 105 |
| $C_2H_5$ | $CH_3O$ | H | H | (A) | 17.2 | 14.0 | 147 |
| $C_2H_5$ | Cl | H | H | (A) | 20.0 | 16.0 | 140 |
| $C_2H_5$ | H | Cl | H | (A) | 18.5 | 12.3 | 149 |
| $C_2H_5$ | H | H | Cl | (A) | 19.3 | 16.8 | 162 |
| $C_2H_5$ | H | H | Br | (A) | 21.5 | 19.2 | 141 |
| $C_2H_5$ | H | Cl | Cl | (B) | 18.3 | 14.0 | 157 |
| $C_2H_5$ | Cl | H | Br | (B) | 24.5 | 16.3 | 166 |
| $C_2H_5$ | H | $CH_3$ | Br | (B) | 20.9 | 17.5 | 140 |
| Cl~$C_2H_4$ | H | H | Cl | (A) | 15.2 | 8.7 | 144 |
| n-$C_3H_7$ | H | H | H | (A) | 18.2 | 10.0 | 117 |
| n-$C_3H_7$ | H | Cl | H | (A) | 19.0 | 9.4 | 110 |

Table 2-continued

| $R^1$ | $R^2$ | $R^3$ | $R^4$ | Method | Yield, g. crude product | Yield, g. purified product | M.p. °C (after re-crystall.) |
|---|---|---|---|---|---|---|---|
| n-$C_3H_7$ | H | H | Cl | (A) | 17.5 | 8.7 | 146 |
| n-$C_3H_7$ | H | H | Br | (A) | 25.0 | 17.5 | 165 |
| i-$C_3H_7$ | H | H | H | (A) | 19.4 | 12.6 | 100 |
| i-$C_3H_7$ | Cl | H | H | (A) | 23.0 | 16.4 | 115 |
| i-$C_3H_7$ | H | Cl | H | (A) | 20.0 | 14.6 | 158 |
| i-$C_3H_7$ | H | H | Cl | (A) | 18.5 | 10.4 | 155 |
| i-$C_3H_7$ | H | H | Br | (A) | 24.4 | 18.6 | 170 |
| n-$C_4H_9$ | H | H | H | (A) | 19.0 | 16.4 | 77 |
| n-$C_4H_9$ | $CH_3$ | H | H | (A) | 20.2 | 10.5 | 90 |
| n-$C_4H_9$ | H | $CH_3$ | H | (A) | 19.4 | 10.0 | 64 |
| n-$C_4H_9$ | H | H | $CH_3$ | (A) | 19.8 | 14.2 | 109 |
| n-$C_4H_9$ | $CH_3O$ | H | H | (A) | 21.6 | 19.2 | 114 |
| n-$C_4H_9$ | Cl | H | H | (A) | 20.0 | 8.4 | 96 |
| n-$C_4H_9$ | H | Cl | H | (A) | 22.4 | 16.0 | 106 |
| n-$C_4H_9$ | H | H | Cl | (A) | 16.8 | 10.2 | 132 |
| n-$C_4H_9$ | H | H | Br | (A) | 26.6 | 18.0 | 142 |
| n-$C_4H_9$ | H | Cl | Cl | (B) | 21.2 | 17.5 | 101 |
| n-$C_4H_9$ | Cl | H | Br | (B) | 23.0 | 15.4 | 117 |
| n-$C_4H_9$ | H | Cl | Br | (B) | 26.0 | 24.6 | 134 |
| n-$C_4H_9$ | $CH_3$ | H | Br | (B) | 26.0 | 24.8 | 105 |
| n-$C_4H_9$ | H | $CH_3$ | Br | (B) | 27.0 | 24.4 | 121 |
| n-$C_4H_9$ | $NO_2$ | H | H | (B) | 24.0 | 15.2 | 83 |
| n-$C_4H_9$ | H | $NO_2$ | H | (B) | 21.0 | 12.6 | 126 |
| n-$C_4H_9$ | H | H | $NO_2$ | (B) | 23.1 | 18.4 | 149 |
| i-$C_4H_9$ | H | H | H | (A) | 19.8 | 14.4 | 135 |
| i-$C_4H_9$ | H | H | $CH_3$ | (A) | 18.8 | 13.4 | 84 |
| i-$C_4H_9$ | H | H | $CH_3$ | (A) | 18.8 | 13.4 | 84 |
| i-$C_4H_9$ | Cl | H | H | (A) | 21.1 | 15.2 | 76 |
| i-$C_4H_9$ | H | Cl | H | (A) | 20.8 | 15.2 | 143 |
| i-$C_4H_9$ | H | H | Cl | (A) | 20.5 | 12.9 | 114 |
| i-$C_4H_9$ | H | H | Br | (A) | 22.5 | 17.6 | 141 |
| n-$C_5H_{11}$ | H | H | H | (A) | 21.0 | 10.0 | 87 |
| n-$C_5H_{11}$ | H | H | $CH_3$ | (A) | 21.2 | 12.2 | 91 |
| n-$C_5H_{11}$ | H | Cl | H | (A) | 20.8 | 10.2 | 89 |
| n-$C_5H_{11}$ | H | H | Cl | (A) | 19.7 | 11.1 | 91 |
| n-$C_5H_{11}$ | H | H | Br | (A) | 18.2 | 15.2 | 127 |
| n-$C_5H_{11}$ | H | Cl | Cl | (B) | 15.8 | 7.6 | 115 |
| n-$C_5H_{11}$ | H | Cl | Br | (B) | 14.9 | 8.5 | 111 |
| n-$C_5H_{11}$ | H | $CH_3$ | Br | (B) | 25.6 | 11.4 | 104 |
| i-$C_5H_{11}$ | H | H | H | (A) | 21.0 | 10.2 | 86 |
| i-$C_5H_{11}$ | H | H | $CH_3$ | (A) | 22.4 | 12.4 | 91 |
| i-$C_5H_{11}$ | H | Cl | H | (A) | 20.8 | 8.4 | 98 |
| i-$C_5H_{11}$ | H | H | Cl | (A) | 15.5 | 5.7 | 93 |
| i-$C_5H_{11}$ | H | H | Br | (A) | 26.0 | 16.4 | 106 |
| i-$C_5H_{11}$ | H | Cl | Cl | (B) | 12.7 | 4.8 | 122 |
| i-$C_5H_{11}$ | H | Cl | Br | (B) | 17.5 | 8.8 | 124 |
| i-$C_5H_{11}$ | H | $CH_3$ | Br | (B) | 16.9 | 8.5 | 113 |
| n-$C_6H_{13}$ | H | H | H | (A) | 16.4 | 9.6 | 74 |
| n-$C_6H_{13}$ | H | H | $CH_3$ | (A) | 24.2 | 15.3 | 80 |
| n-$C_6H_{13}$ | H | Cl | H | (A) | 15.8 | 8.2 | 89 |
| n-$C_6H_{13}$ | H | H | Cl | (A) | 12.4 | 6.3 | 108 |
| n-$C_6H_{13}$ | H | H | Br | (A) | 27.4 | 16.0 | 120 |
| n-$C_6H_{13}$ | H | Cl | Cl | (B) | 21.2 | 7.8 | 100 |
| n-$C_6H_{13}$ | H | Cl | Br | (B) | 20.0 | 6.8 | 102 |
| n-$C_6H_{13}$ | H | $CH_3$ | Br | (B) | 27.8 | 12.5 | 98 |
| n-$C_7H_{15}$ | H | H | Cl | (A) | 17.6 | 8.5 | 105 |
| n-$C_8H_{17}$ | H | H | Cl | (A) | 19.5 | 6.8 | 105 |
| n-$C_9H_{19}$ | H | H | Cl | (A) | 20.5 | 6.0 | 96 |
| n-$C_{10}H_{21}$ | H | H | Cl | (A) | 17.3 | 5.7 | 95 |
| n-$C_{12}H_{25}$ | H | H | Cl | (A) | 18.5 | 4.9 | 93 |

EXAMPLE 2

Powder mixtures of the following compositions are prepared by admixing the respective ingredients with each other:

| | |
|---|---|
| one or more active agent of the formula (I) | 1 to 95% |
| talo | 99 to 5% |

The obtained powder mixtures can be used directly as powder dusts in the plant protection.

EXAMPLE 3

Wettable powder mixtures of the following compositions are prepared by admixing the respective ingredients with each other:

| | |
|---|---|
| one or more active agent of the formula (I) | 10 to 60% |
| kaoline, talc, chalk powder and/or clay | 89 to 25% |
| wetting and/or dispersing agents (e.g. alkylated benzene- or naphthalenesulfonates, fatty alcohol sulfonates, sulfonated fatty acid esters, polyoxyethylene-fatty alcohol ethers, polyoxyethylene-fatty acid esters, sodium sulfosuccinate esters, sulfonated mineral oils, sulfonated vegetable oils, methyl cellulose, polyvinyl alchohol, sodium calcium or magnesium ligninsulfonate, sodium naphthalenesulfonate, polyvinylpyrrolidone derivatives, lignin, sulfite waste liquor, etc.) | 1 to 15% |

EXAMPLE 4

Solutions of the following compositions are prepared by admixing the respective ingredients with each other:

| | |
|---|---|
| at least one compound of the formula (I) | 5 to 10% |
| at least one water-miscible solvent (e.g. dimethylformamide, isopropanol, ethanol, methanol | |

| | |
|---|---|
| or acetone) | 95 to 88% |
| wetting and/or dispersing agents (e.g. the compounds listed in Example 3) | 0.1 to 2% |

The obtained solutions can be used as sprays after diluting them with water.

What we claim is:

1. A method of combatting phytopathogenic fungi which comprises applying to a plant infected with the fungi an effective amount of a compound of the formula:

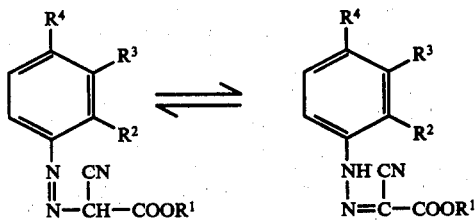

wherein
- $R^1$ is $C_1$ to $_{12}$ alkyl or chloroethyl
- $R^2$ is hydrogen, halogen, $C_1$ to $C_4$ alkyl $C_{1\,to\,4}$ alkoxy or nitro,
- $R^3$ is hydrogen, halogen, $C_{1\,to\,4}$ alkyl or nitro, and
- $R^4$ is hydrogen, halogen, $C_{1\,to\,4}$ alkyl or nitro, or an acid addition salt thereof effective against fungi.

2. The method defined in claim 1 wherein $R^1$ is $C_1$ to $C_4$ alkyl, $R^2$ is hydrogen, and $R^3$ and $R^4$ are each hydrogen, chloro, or nitro.

* * * * *